US011020126B2

(12) United States Patent
Uesaka et al.

(10) Patent No.: US 11,020,126 B2
(45) Date of Patent: Jun. 1, 2021

(54) ENDOSCOPIC SURGICAL DEVICE

(71) Applicant: OLYMPUS CORPORATION, Hachioji (JP)

(72) Inventors: Kensuke Uesaka, Tokyo (JP); Yuta Muyari, Tokyo (JP); Tomohiro Tsuji, Tokyo (JP); Tomohiko Mamiya, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 178 days.

(21) Appl. No.: 16/236,706

(22) Filed: Dec. 31, 2018

(65) Prior Publication Data
US 2019/0133598 A1 May 9, 2019

Related U.S. Application Data

(63) Continuation of application No. PCT/JP2016/070388, filed on Jul. 11, 2016.

(51) Int. Cl.
*A61B 17/12* (2006.01)
*A61B 17/128* (2006.01)
(Continued)

(52) U.S. Cl.
CPC ...... *A61B 17/1285* (2013.01); *A61B 17/1227* (2013.01); *A61B 2017/2929* (2013.01)

(58) Field of Classification Search
CPC ............ A61B 17/1285; A61B 17/1227; A61B 17/128; A61B 17/122; A61B 17/0482;
(Continued)

(56) References Cited

U.S. PATENT DOCUMENTS 5,766,184 A 6/1998 Matsuno et al.
2011/0054498 A1* 3/2011 Monassevitch .... A61B 17/1285
606/142

FOREIGN PATENT DOCUMENTS

EP 2 995 264 A1 3/2016
JP H08-280701 A 10/1996
(Continued)

OTHER PUBLICATIONS

Sep. 20, 2016 International Search Report issued in International Patent Application No. PCT/JP2016/070388.
(Continued)

*Primary Examiner* — Erich G Herbermann
(74) *Attorney, Agent, or Firm* — Oliff PLC

(57) ABSTRACT

An endoscopic surgical device that includes: a sheath; a manipulator; a manipulation wire; a clip body having a pair of arms, connected to a distal end of the manipulation wire, and configured to be capable of advancing and retracting in accordance with manipulation of the manipulator along with a longitudinal axis of the manipulation wire; a holding tube into which a proximal portion of the clip body is inserted to be capable of advancing and retracting; and a biasing member configured to hold a position of the manipulation wire at an initial position. The clip body is nonrotatable around the longitudinal axis at the initial position. When the manipulation wire is advanced a prescribed amount against a biasing force of the biasing member, the clip body is rotatable around the longitudinal axis, and is allowed adjustment of an opening-closing direction of the pair of arms.

11 Claims, 12 Drawing Sheets

(51) Int. Cl.
*A61B 17/122* (2006.01)
*A61B 17/29* (2006.01)

(58) Field of Classification Search
CPC . A61B 17/0487; A61B 17/08; A61B 17/1222;
A61B 2017/2929; A61B 2017/00818;
A61B 2017/00584; A61B 2017/0488;
A61B 2017/049; A61B 2017/1225; A61F 5/0086
See application file for complete search history.

(56) References Cited

FOREIGN PATENT DOCUMENTS

| | | |
|---|---|---|
| JP | 2002-191609 A | 7/2002 |
| JP | 2009-072611 A | 4/2009 |
| JP | 2012-200415 A | 10/2012 |
| JP | 2013-063106 A | 4/2013 |
| JP | 2016-002392 A | 1/2016 |
| WO | 2014/181675 A1 | 11/2014 |

OTHER PUBLICATIONS

Oct. 29, 2019 Japanese Office Action issued in Japanese Patent Application No. 2018-527049.

* cited by examiner

ENDOSCOPIC SURGICAL DEVICE

This application is a continuation application based on PCT Patent Application No. PCT/JP2016/070388, filed Jul. 11, 2016, the content of which is incorporated herein by reference.

BACKGROUND OF THE INVENTION

Field of the Invention

The present invention relates to an endoscopic surgical device that is inserted into a body and is used to ligate a tissue.

Description of the Related Art

A clip device that ligates a target tissue for treatment with a clip inserted into a body through an endoscopic device in order to perform closure of an opening caused in a biological tissue, hemostasis treatment, or the like has been known. For example, a clip device in which a clip unit, which includes a clip, a holding tube, and a coupler, is connected to a manipulation wire provided to be capable of advancing and retracting in a sheath, and mounting and ligating manipulations of the clip unit are performed by the advance and retract of a manipulation member is disclosed in Japanese Unexamined Patent Application, First Publication No. 2002-191609. In the endoscopic device of Japanese Unexamined Patent Application, First Publication No. 2002-191609, when a proximal portion of the clip is pulled into a holding tube, a pair of arms positioned at a distal end side of the clip approach each other to be closed to grasp the target tissue for ligation. Afterward, the clip unit is disconnected from the endoscopic device, and is indwelled in the target tissue for treatment.

In the conventional endoscopic surgical device, it is sometimes desired to adjust a direction in which the target tissue targeted for ligation is grasped by the clip. An endoscopic surgical device that includes a rotation control mechanism for aligning a direction around a longitudinal axis of the surgical device to a desired position and rotates the surgical device around the longitudinal axis is disclosed in Japanese Unexamined Patent Application, First Publication No. 2012-200415.

SUMMARY OF THE INVENTION

An endoscopic surgical device according to a first aspect of the present invention includes: a sheath; a manipulator provided at a proximal end of the sheath; a manipulation wire whose proximal end is coupled to the manipulator and which is inserted through the sheath; a clip body having a pair of openable and closeable arms and connected to a distal end of the manipulation wire, the clip body being configured to be capable of advancing and retracting in accordance with manipulation of the manipulator in a direction of a longitudinal axis of the manipulation wire; a holding tube into which a proximal portion of the clip body is inserted to be capable of advancing and retracting; and a biasing member configured to hold a position of the manipulation wire at an initial position. The clip body is not rotatable around the longitudinal axis at the initial position. When the manipulation wire is advanced by a prescribed amount against a biasing force of the biasing member, the clip body is rotatable around the longitudinal axis, and is allowed an opening-closing direction of the pair of arms to be adjusted.

According to a second aspect of the present invention, in the endoscopic surgical device according to the first aspect, when the clip body is rotatable around the longitudinal axis, the holding tube may be locked onto the clip body so as to rotate while following a rotation of the clip body.

According to a third aspect of the present invention, in the endoscopic surgical device according to the second aspect, the biasing member may be disposed at a distal portion of the sheath.

According to a fourth aspect of the present invention, the endoscopic surgical device according to the second aspect may further include: a tubular member to which a distal end of the biasing member is connected and through which the manipulation wire is inserted; and a convex portion provided to protrude from an outer circumference of the manipulation wire. A proximal end of the biasing member may be fixed to the distal portion of the sheath. The convex portion and the tubular member may come into contact with each other when the manipulation wire is advanced and retracted, and the distal end of the biasing member may advance and retract.

According to a fifth aspect of the present inventions, the endoscopic surgical device according to the third aspect may further include: a tubular member to which a distal end of the biasing member is connected and through which the manipulation wire is inserted; and a convex portion provided to protrude from an outer circumference of the manipulation wire. A proximal end of the biasing member may be fixed to the distal portion of the sheath. The convex portion and the tubular member may come into contact with each other when the manipulation wire is advanced and retracted, and the distal end of the biasing member may advance and retract.

According to a sixth aspect of the present invention, in the endoscopic surgical device according to the first aspect, when the clip body is rotatable around the longitudinal axis, the holding tube may be locked onto a distal portion of the sheath to be nonrotatable around the longitudinal axis.

According to a seventh aspect of the present invention, in the endoscopic surgical device according to the fifth aspect, the manipulator may include: a manipulator body; and a slider which is slidable relative to the manipulator body and to which the manipulation wire is coupled. The biasing member may be provided in the manipulator body, bias the slider toward a proximal end side, and thereby hold the position of the manipulation wire at the initial position.

DETAILED DESCRIPTION OF THE INVENTION

First Embodiment

Figure 1:
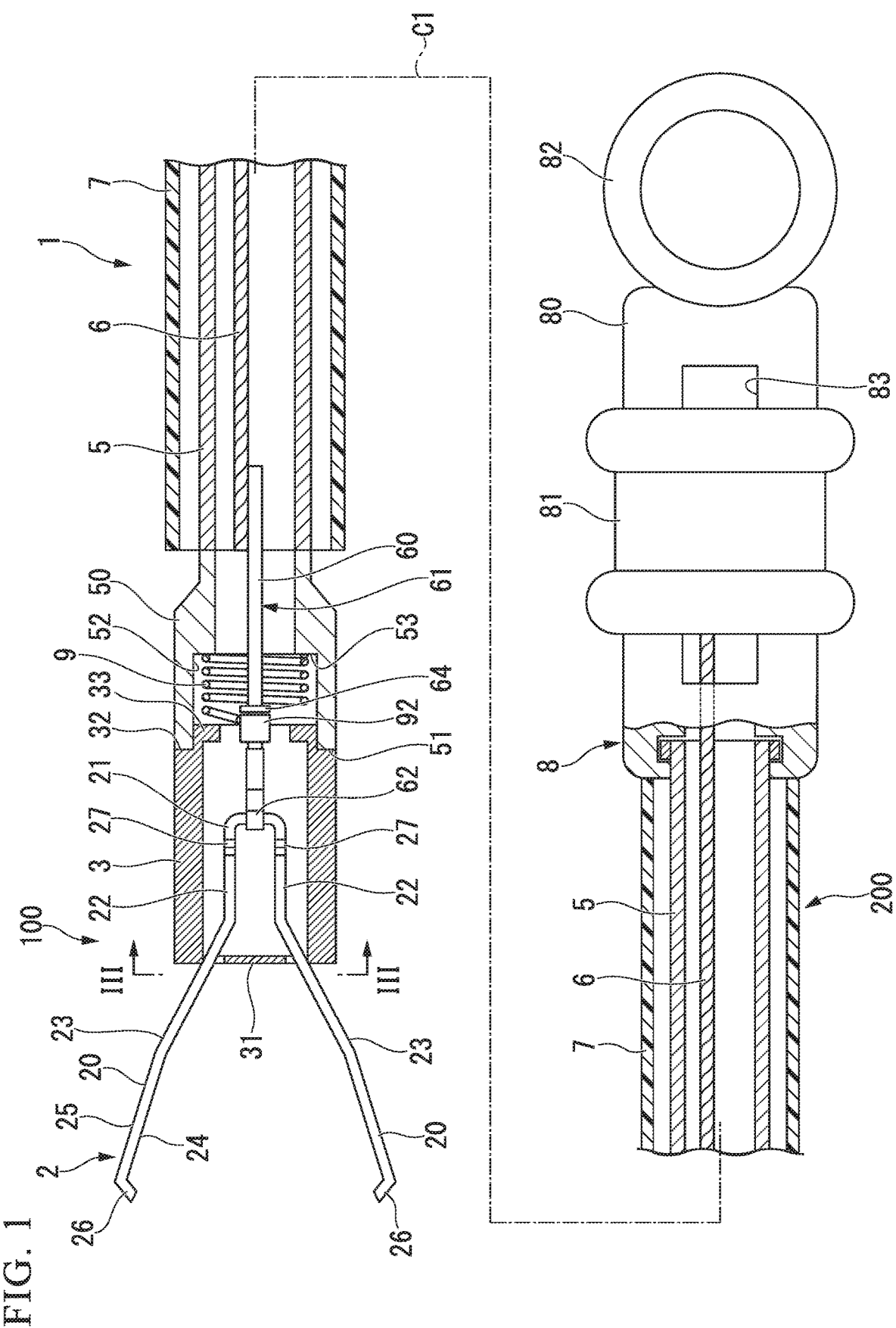
FIG. 1 is a sectional view of an endoscopic surgical device according to a first embodiment of the present invention.
Figure 2:
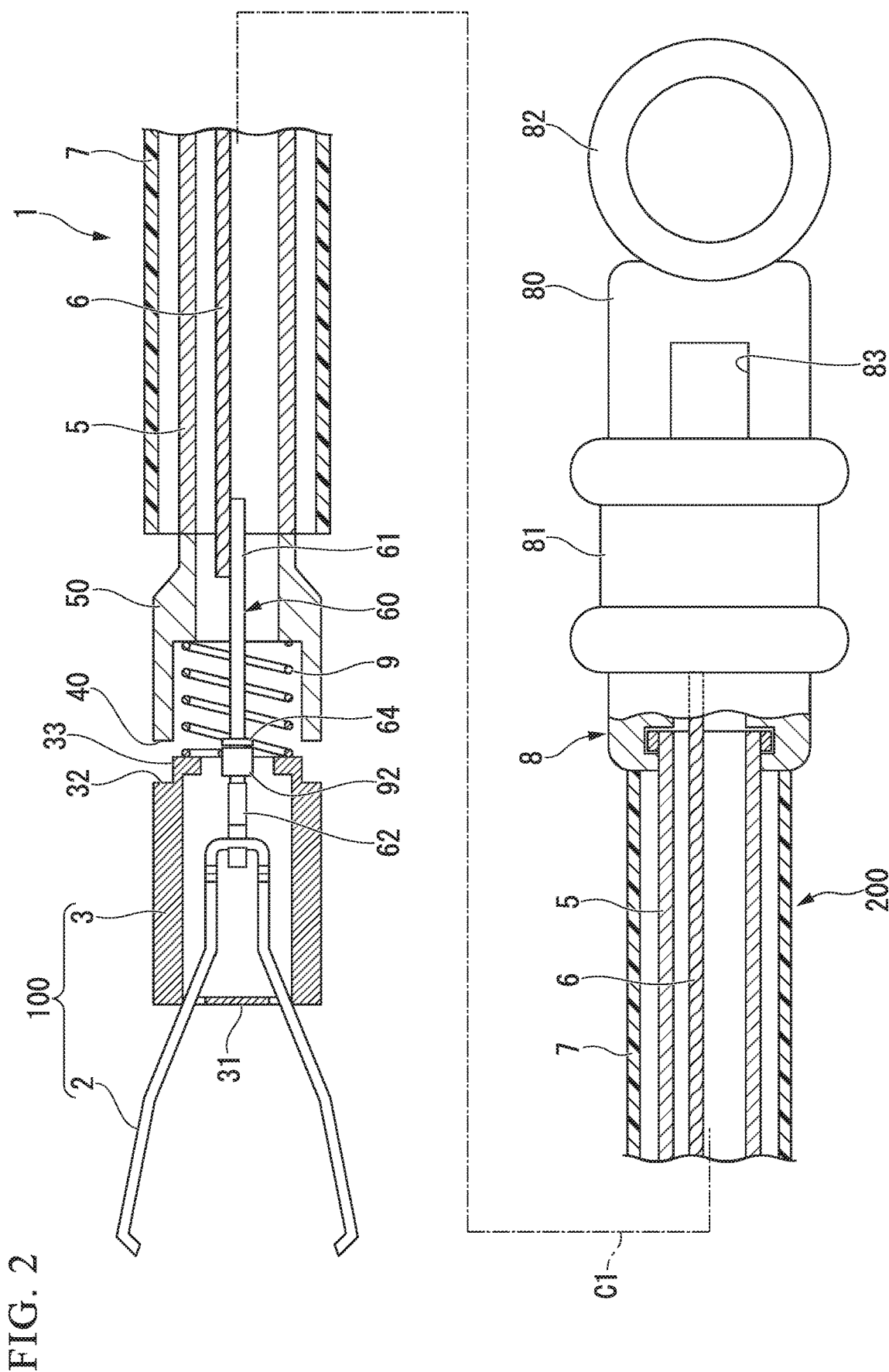
FIG. 2 is a sectional view of the endoscopic surgical device according to the first embodiment of the present invention.

Hereinafter, a first embodiment of an endoscopic surgical device according to the present invention will be described with reference to FIGS. 1 to 6. FIGS. 1 and 2 are sectional views of the endoscopic surgical device 1 according to the present embodiment. As illustrated in FIGS. 1 and 2, the endoscopic surgical device 1 includes a clip body 2, a holding tube 3, a coil sheath (a sheath) 5, a manipulation wire 6, a sheath tube 7, a manipulator 8, and a coil spring (a biasing member) 9. The clip body 2 and the holding tube 3 constitute a clip unit 100, and the coil sheath 5, the manipulation wire 6, the sheath tube 7, the manipulator 8, and the coil spring 9 constitute a surgical device body 200. The endoscopic surgical device 1 is a device that indwells the clip unit 100 in a body using the surgical device body 200.

In the following description, a central line in a longitudinal direction in the state in which the endoscopic surgical device 1 extends in a linear shape is referred to as a longitudinal axis C1. A side close to the manipulator 8 in the endoscopic surgical device 1 is referred to as a proximal end side, and a side opposite to the proximal end side in the direction of the longitudinal axis C1 and on which the clip body 2 is provided is referred to as a distal end side.

Parts of the surgical device body 200 will be described. The sheath tube 7 is a tubular member having flexibility. For example, a resin material such as a fluorine resin such as polytetrafluoroethylene (PTFE) or high-density polyethylene (HDPE) can be used as a material of the sheath tube 7.

The coil sheath 5 is a tubular member having flexibility, and is inserted through the sheath tube 7. The coil sheath 5 is formed by densely winding strands formed of, for example, stainless steel such as SUS301 in the direction of the longitudinal axis C1.

The coil sheath 5 includes a sheath distal end member 50. The sheath distal end member 50 is an approximately cylindrical member, is disposed coaxially with the coil sheath 5, and is joined to a distal end of the coil sheath 5.

A distal end side of a lumen of the sheath distal end member 50 is increased in diameter, and a coil housing 52 for housing the coil spring 9 is formed. Thereby, a wall 53 that is perpendicular to the longitudinal axis C1 and faces a distal side is formed at a proximal portion of the coil housing 52.

The manipulation wire 6 is formed of a metal single wire or stranded wire, and is inserted into the coil sheath 5. A proximal end of the manipulation wire 6 is fixed to a slider 81, and a coupler 61 is fixed to a distal end of the manipulation wire 6.

The coupler 61 is a member that couples the clip body 2 and the manipulation wire 6 together. The distal end of the manipulation wire 6 is connected to the clip body 2 via the coupler 61. The distal end of the manipulation wire 6 and a proximal portion of the coupler 61 are joined by welding or the like. A hook 62 is provided at a distal portion of the coupler 61. The proximal portion 60 of the coupler 61 is formed in a rod shape, and an annular convex portion 64 that protrudes from an outer circumference in a circumferential direction is fixed to the coupler 61. An outer diameter of the convex portion 64 is larger than an outer diameter of a tubular member 92.

The tubular member 92 is disposed between the convex portion 64 of the manipulation wire 6 and the hook 62 of the coupler 61. The tubular member 92 has an inner diameter that does not have an influence on a rotating operation of the coupler 61 around the longitudinal axis C1. The proximal portion 60 of the coupler 61 is inserted into the tubular member 92 and the coil spring 9 in the direction of the longitudinal axis C1. The proximal portion 60 of the coupler 61 is capable of advancing and retracting and rotatable relative to the tubular member 92. For this reason, the tubular member 92 and the coil spring 9 do not obstruct advance and retraction or rotation of the coupler 61.

As illustrated in FIG. 1, the coil spring 9 is housed in the coil housing 52 of the sheath distal end member 50. A proximal end of the coil spring 9 is joined to the wall 53 of the coil housing 52. A distal end of the coil spring 9 is joined to an outer circumferential surface of the tubular member 92.

The manipulator 8 is provided on proximal ends of the sheath tube 7 and the coil sheath 5. The manipulator 8 includes a manipulator body 80 and a slider 81.

The manipulator body 80 is formed in a rod shape that extends in the direction of the longitudinal axis C1, and a finger hook 82 is provided at a proximal portion of the manipulator body 80.

The slider 81 is mounted on the manipulator body 80 to be slidable in the direction of the longitudinal axis C1. A slide groove 83 that extends in the direction of the longitudinal axis C1 is provided in the manipulator body 80.

A proximal end of the sheath tube 7 is in contact with the manipulator body 80, and is provided to be capable of advancing and retracting and rotatable relative to the manipulator 8. A proximal end of the coil sheath 5 is connected to the manipulator body 80 so as to be rotatable and not to be advancable and retractable relative to the manipulator body 80.

Next, parts of the clip unit 100 will be described.

The clip body 2 includes a pair of arms 20 and a connector 21 positioned on a proximal end of the clip body 2. As illustrated in FIG. 1, the clip body 2 is formed to be linearly symmetrical with respect to the longitudinal axis C1 of the holding tube 3. In the clip body 2, the connector 21 is formed by bending the middle of a thin elongated plate made of, for example, a metal such as stainless steel, a cobalt chromium alloy, titanium, or the like, and opposite ends of the thin elongated plate become the pair of arms 20. The pair of arms 20 has bases 22 that extend in parallel from the connector 21 toward a distal side, and expanded parts 23 that are located on a more distal side than the bases 22 and tend to bend away from each other toward the distal side in a natural state. In the following description, in the pair of arms 20, surfaces that face each other are referred to as inner surfaces 24, and surfaces that are opposite to the inner surfaces 24 and face an inner surface of the holding tube 3 are referred to as outer surfaces 25. Distal portions of the pair of arms 20 (distal ends of the expanded parts 23) are bent toward the inner surfaces 24 to form claws 26.

Figure 3:
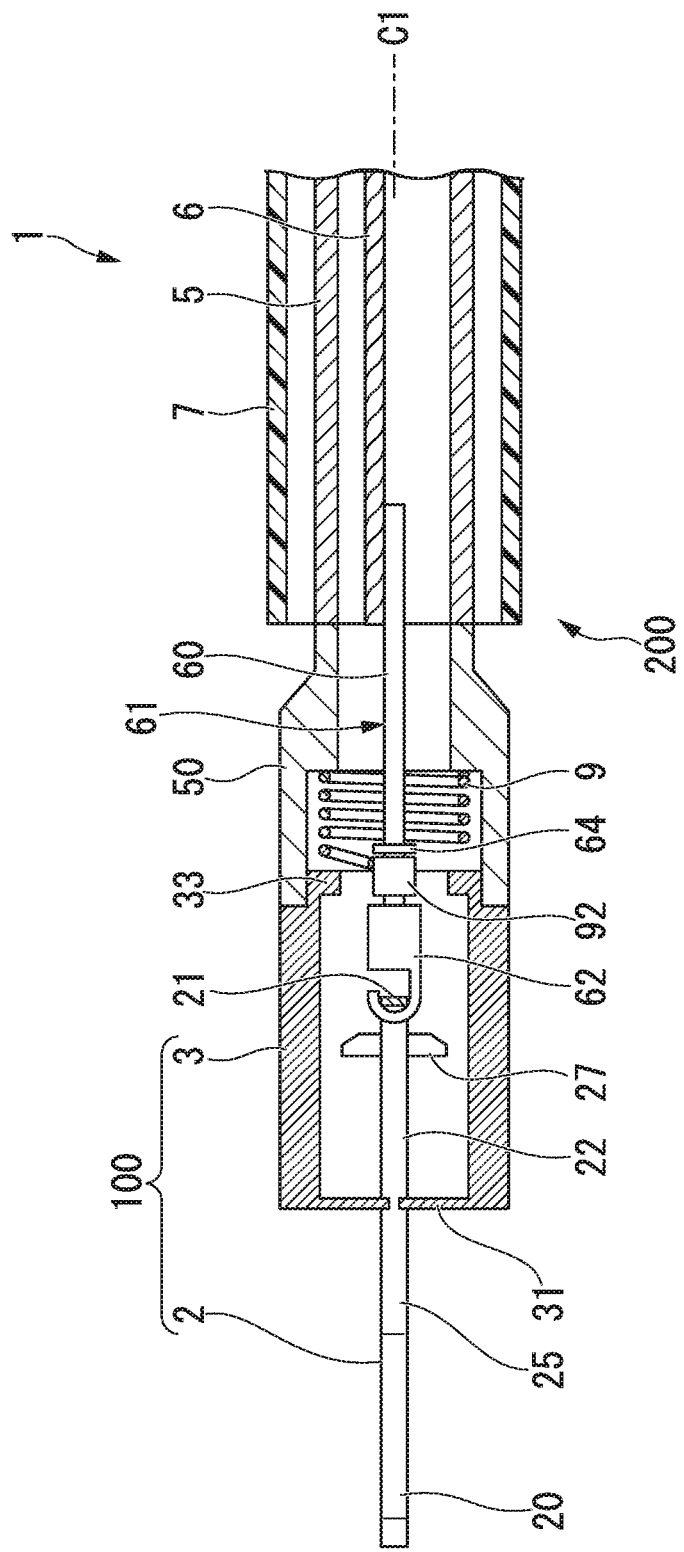
FIG. 3 is a sectional view of a distal portion of the endoscopic surgical device according to the first embodiment of the present invention.

FIG. 3 is a sectional view of the distal portion of the endoscopic surgical device 1 when viewed in an opening-closing direction of the pair of arms 20. The clip body 2 includes stoppers 27 that are formed integrally with the clip body 2. The stoppers 27 are provided for fixing the clip body 2 to the holding tube 3 when the clip unit 100 is indwelled. As illustrated in FIG. 3, the stoppers 27 are formed to protrude and extend from both sides of the bases 22 in a direction perpendicular to the longitudinal axis C1. When viewed from the outer surfaces 25 of the clip body 2, the stoppers 27 are formed to extend to be linearly symmetrical to each other with respect to the longitudinal axis C1. Lengths of the stoppers 27 in the direction perpendicular to the longitudinal axis C1 are slightly larger than an opening diameter of a proximal end annular part of the holding tube 3 (to be described below).

Figure 4:
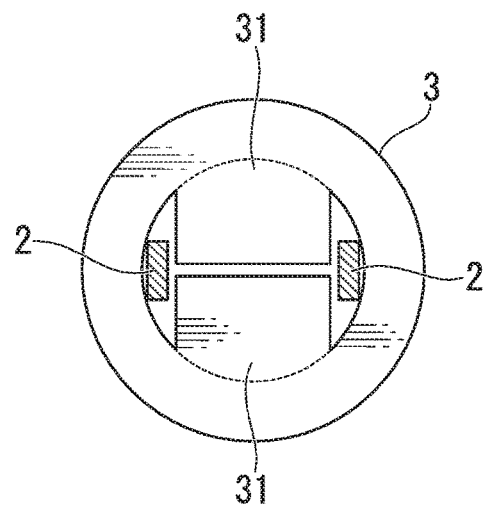
FIG. 4 is a sectional view of the endoscopic surgical device taken along line III-III of FIG. 1.

FIG. 4 is a sectional view of the endoscopic surgical device along a line of FIG. 1. The holding tube 3 is a tubular member that is capable of housing a proximal portion of the clip body 2. Here, the proximal portion of the clip body 2 is a portion that includes the connector 21, the bases 22 of the arms 20, and parts of the proximal end sides of the expanded parts 23 of the arms 20.

As illustrated in FIG. 4, a covering part 31 is provided at a distal portion of the holding tube 3. The covering part 31 is provided to extend inward from an edge of a distal end opening of the holding tube 3 in the radial direction and to cover approximately the middle of the distal end opening of the holding tube 3. A region through which the pair of arms 20 is inserted is not covered by the covering part 31.

The proximal portion of the clip body 2 is housed in the holding tube 3. Since the covering part 31 covers the distal end opening of the holding tube 3, the clip body 2 does not rotate around the longitudinal axis C1 relative to the holding tube 3. As a result, the holding tube 3 is locked with the clip body 2 to rotate while following the rotation of the clip body 2 around the longitudinal axis C1.

Figure 5:
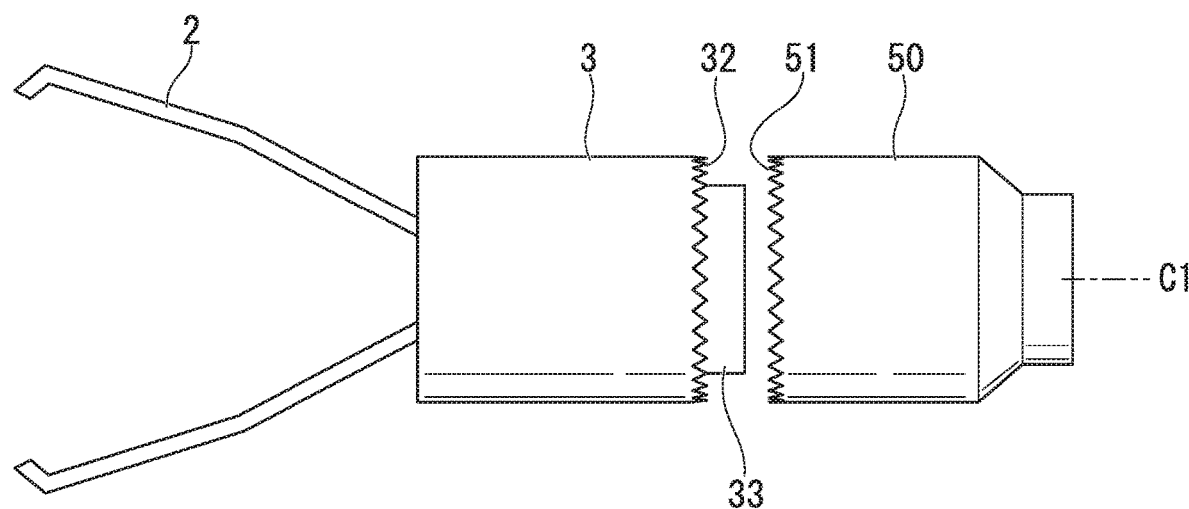
FIG. 5 is a side view of a holding tube and a sheath distal end member of FIG. 1.

FIG. 5 is a side view of the holding tube 3 and the sheath distal end member 50. A distal end face 51 of the sheath distal end member 50 has a shape that is indented in the direction of the longitudinal axis C1. As illustrated in FIG. 5, a proximal end face 32 of the holding tube 3 is indented in the direction of the longitudinal axis C1 of the holding tube 3, and has an indented shape that meshes with the indented shape of the distal end face 51 of the sheath distal end member 50.

A proximal end annular part 33 inserted into a distal end opening of the sheath distal end member 50 is formed on a proximal part of the holding tube 3. The proximal end annular part 33 is positioned at more proximal side than the proximal end face 32 of the holding tube 3. As illustrated in FIG. 1, the proximal end annular part 33 has an outer diameter that allows insertion into the opening of the sheath distal end member 50, and has an inner diameter that is smaller than that of a lumen of the distal end side of the holding tube 3.

In the present embodiment, the proximal end annular part 33 enters the distal end opening of the sheath distal end member 50, and the proximal end face 32 of the holding tube 3 is meshed with the distal end face 51 of the sheath distal end member 50. Thereby, the holding tube 3 is locked with the coil sheath 5 so as not to be rotatable relative to the coil sheath 5.

The holding tube 3 is made, for example, using a metal material such as stainless steel, a titanium alloy (Ti-6Al-4V or the like), a cobalt chromium alloy, or the like, or a high-rigidity resin material having moderate elasticity such as polyphthalamide (PPA), polyamide (PA), or the like.

As described above, in the endoscopic surgical device 1, the manipulation wire 6 is inserted into the sheath tube 7 and the coil sheath 5, and the connector 21 of the clip body 2 is locked on the hook 62 at a position more distal side than the coil spring 9 and the tubular member 92. The manipulation wire 6 is capable of advancing and retracting in the sheath tube 7, the coil sheath 5, and the holding tube 3 in the direction of the longitudinal axis C1 by operating of the advance and retraction of the slider 81, and the clip body 2 is configured to advance and retract in the direction of the longitudinal axis C1 in accordance with the advance and retraction of the manipulation wire 6.

In the natural state in which no external load is applied to the endoscopic surgical device 1, the manipulation wire 6 is held at an initial position by the coil spring 9. At the initial position, the clip body 2 is in a nonrotatable state (the state illustrated in FIG. 1) in which it cannot rotate around the longitudinal axis C1. In the present embodiment, a state in which the holding tube 3 is nonrotatably locked on the sheath distal end member 50 is considered an initial state. In the natural state, the coil spring 9 biases the manipulation wire 6 toward the proximal side such that the initial state is maintained. To be specific, the tubular member 92 is pulled toward the proximal end side by a biasing force of the coil spring 9, and presses the convex portion 64 toward the proximal end side, so that the manipulation wire 6 is held at a prescribed position. That is, the manipulation wire 6 is configured to be held at a prescribed position by the tubular member 92, the convex portion 64, and the length and the biasing force of the coil spring 9.

Meanwhile, when the manipulation wire 6 is advanced a prescribed amount against the biasing force of the coil spring 9 by manipulation of the slider 81, the clip body 2 and the holding tube 3 advance relative to the sheath distal end member 50. The holding tube 3 is rotatable around the longitudinal axis C2 while following the advance of the clip body 2, and thus the endoscopic surgical device 1 is put in a rotatable state (a state illustrated in FIG. 2) in which an opening-closing direction of the clip body 2 to be in adjustable. To be specific, the coil spring 9 is configured to extend toward the distal side when the manipulation wire 6 advances by manipulation of the slider 81 by an operator and the tubular member 92 is pushed toward the distal side by the convex part 64. When a load of a force toward the slider 81 is released, for example, the operator relaxes a force for applying a load to the slider 81 after the advance and retraction of the slider 81, the clip body 2 returns to the nonrotatable state by the biasing force of the coil spring 9.

Next, with regard to an operation of the endoscopic surgical device 1, a procedure in which the clip unit 100 is indwelled in the body using the endoscopic surgical device 1 will be described by way of example.

First, the operator inserts an insertion part of an endoscope into a body, and moves it forward toward the target tissue for treatment. Then, the operator inserts the endoscopic surgical device 1 in an initial state in which the clip unit 100 is housed in the sheath tube 7 from a proximal portion of a channel of the endoscope, and causes the sheath tube 7 to protrude from a distal end of the insertion part. Furthermore, the operator causes the clip unit 100 to protrude from the sheath tube 7.

The endoscopic surgical device 1 in the initial state is in the natural state in which no external load is applied to the endoscopic surgical device 1, and in a state in which the manipulation wire 6 is held at the initial position. The initial state of the endoscopic surgical device 1 is a state in which the clip body 2 is incapable of rotating relative to the coil sheath 5 and the sheath distal end member 50 (a state in which the clip body 2 is incapable of rotating around the longitudinal axis C1).

Next, the operator advances the manipulation wire 6 by advancing the slider 81. When the manipulation wire 6 is advanced, the clip body 2 is advanced. Since the holding tube 3 is locked on the clip body 2 by the covering part 31, the holding tube 3 advances by following the advance of the clip body 2. The holding tube 3 advances toward the distal side relative to the sheath distal end member 50, and the clip body 2 and the holding tube 3 are put in a state in which they can be rotated around the longitudinal axis C1.

Next, a position of the clip body 2 around the longitudinal axis C1 is adjusted. The operator rotates the manipulator 8 around the longitudinal axis C1 while holding the proximal portion of the coil sheath 5, and rotates the clip body 2 relative to the coil sheath 5 by transmitting a driving force for rotation via the manipulation wire 6. Due to this manipulation, the clip body 2 and the holding tube 3 rotate relative to the coil sheath 5, and thus the operator adjusts the arms 20 to a desired position.

Next, the operator makes the clip body 2 be in a nonrotatable state. When the operator relaxes a force applied to the slider 81, the tubular member 92 moves toward the proximal end side due to a restoring force of the coil spring 9 and presses the convex portion 64 toward the proximal side, and the manipulation wire 6 retracts toward the proximal side up to the initial position. When the manipulation wire 6 retracts to the initial position, the proximal end annular part 33 of the holding tube 3 enters the distal end of the sheath distal end member 50, the proximal end face 32 of the holding tube 3 and the distal end face 51 of the sheath distal end member 50 are meshed, and the clip body 2 and the holding tube 3 cannot rotate around the longitudinal axis C1. Thereby, the clip unit 2 do not rotate even when they receive a reaction force from the tissue to be treated.

Next, in a state in which the claws 26 of the clip body 2 are pressed against the tissue to be treated, the operator pulls the slider 81 toward the proximal side while holding the manipulator body 80. Then, the manipulation wire 6 is pulled toward the proximal side relative to the initial position, and the clip body 2 retracts relative to the holding tube 3. As a result, the expanded parts 23 of the arms 20 advance into the holding tube 3, and the claws 26 approach each other, so that the tissue can be ligated by the arms 20.

When the operator further pulls the slider 81 toward the proximal side after the target tissue for treatment is ligated, the stoppers 27 retract toward the proximal side while being bent and in contact with the inner circumferential surface of the proximal end annular part 33 of the holding tube 3. The bending of the stoppers 27 is released after the stoppers 27 reach the proximal end side relative to the proximal end annular part 33, and the distal end faces of the stoppers 27 comes into contact with the proximal end face of the proximal end annular part 33 so that the clip body 2 is engaged with the holding tube 3 (see FIG. 6). In this case, a distance between the arms 20 becomes shortest.

Figure 6:
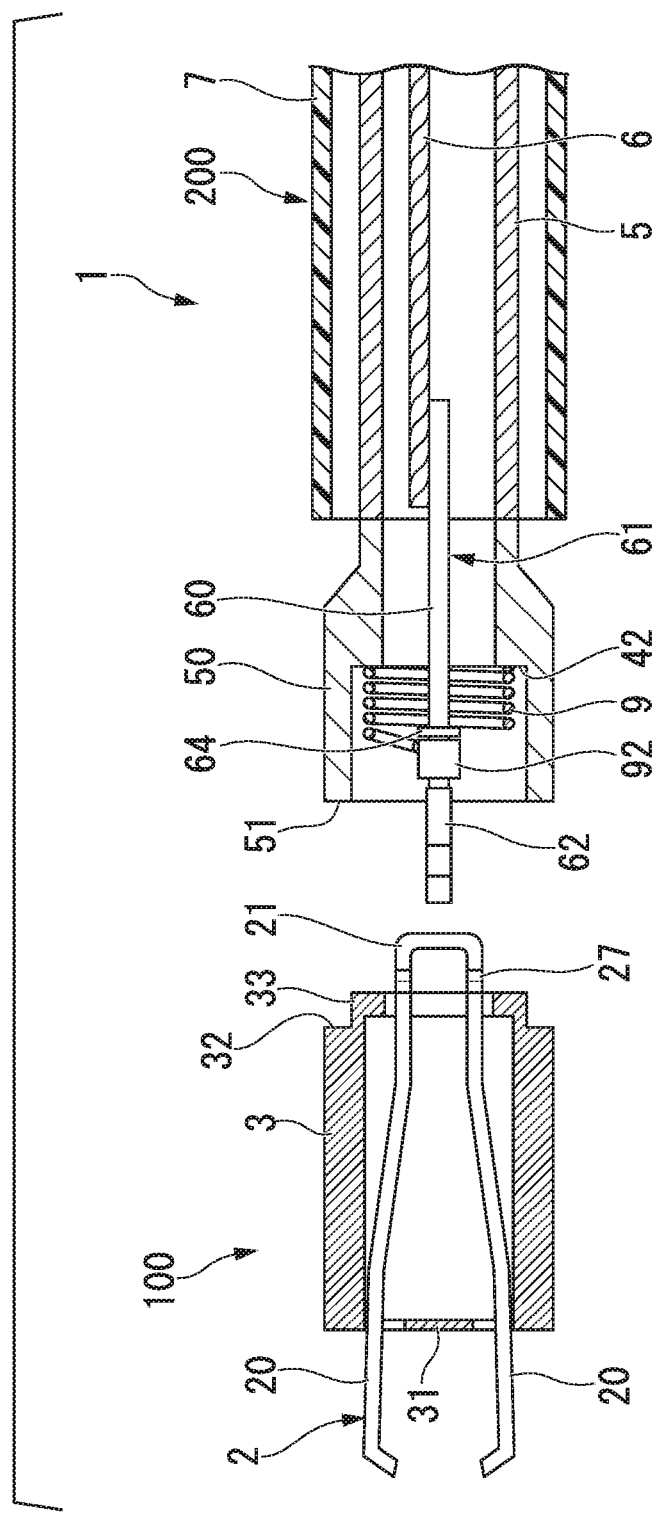
FIG. 6 is a view illustrating a use mode of the endoscopic surgical device according to the first embodiment of the present invention.

When the slider 81 is further pulled toward the proximal end side after the clip body 2 is engaged with the holding tube 3, the manipulation wire 6 retracts, but the clip body 2 does not retract. For this reason, a tensile load is applied to the hook 62, and the hook 62 is deformed. The connector 21 of the clip body 2 is unlocked, and the coupler 61 and the clip body 2 are uncoupled as illustrated in FIG. 6. In this case, the coil spring 9 returns to an unloaded state from a state in which the coil spring 9 is compressed toward the proximal side. As a result, the clip unit 100 is separated from the surgical device body 200 and is indwelled in the body.

Next, the operator pulls the slider 81 to store the coupler 61 in the coil sheath 5. Furthermore, after the surgical device body 200 is removed from the insertion part of the endoscope, the insertion part of the endoscope is removed from the body of a patient, and the procedure is completed.

In the endoscopic surgical device 1 according to the present embodiment, the clip body 2 and the holding tube 3 are held to be nonrotatable relative to the coil sheath 5 around the longitudinal axis C1 in the natural state in which no load is applied to the slider 81. Therefore, manipulating the clip body 2 to rotate around the longitudinal axis C1 to in a desired direction is easily performed, and the clip body 2 is prevented from being rotated by receiving an external force after the opening-closing direction of the pair of arms 20 is adjusted.

In the endoscopic surgical device 1 according to the present embodiment, as in the case where the claws of the clip body 2 comes into contact with the target tissue for treatment, the clip body 2 is prevented from being rotated by receiving an external force to the distal end of the clip body 2. Meanwhile, when the slider 81 is advanced, and the clip body 2 and the holding tube 3 are moved from the coil sheath 5 toward the distal side, the clip body 2 is allowed to be rotatable around the longitudinal axis C1. For this reason, the endoscopic surgical device 1 according to the present embodiment is capable of switching the clip body 2 between the rotatable state and the nonrotatable state by simple manipulation called the advance and retraction of the manipulation wire 6, and the direction of the clip body 2 is also easily adjusted. That is, the endoscopic surgical device 1 has excellent manipulability.

In the endoscopic surgical device 1 according to the present embodiment, the coil spring 9 is disposed between the proximal end of the holding tube 3 and the distal end of the sheath distal end member 50 (the distal portion of the sheath). As a result, since a biasing force caused by the coil spring 9 is transmitted in the vicinity of the clip body 2 and the holding tube 3, the biasing force is sufficiently and quickly transmitted to a small-diameter portion such as a distal portion of the endoscopic surgical device 1. Therefore, the rotatable state and the nonrotatable state of the clip body 2 are also accurately switched by the coil spring 9.

In the endoscopic surgical device 1 according to the present embodiment, since the proximal end of the coil spring 9 is joined to the sheath distal end member 50, and the distal end of the coil spring 9 is connected to the manipulation wire 6 to be capable of advancing in accordance with the advance of the manipulation wire 6, the clip body 2 is capable of being easily switched from the nonrotatable state to the rotatable state. Even after the clip unit 100 is separated from the surgical device body 200, the coil spring 9 does not fall off.

In the endoscopic surgical device 1 according to the present embodiment, the covering part 31 is provided on the holding tube 3, and the covering part 31 and the arms 20 are locked. For this reason, the holding tube 3 is configured to rotate while following the rotation of the clip body 2. The arms 20 are capable of being prevented from being unintentionally closed by the external force toward the distal end sides of the arms 20. Therefore, the clip body 2 is capable of being rotated while the arms 20 are held in a moderately opened state, and easily grasps the target tissue for treatment.

In the endoscopic surgical device 1 according to the present embodiment, the convex portion 64 comes into contact with the tubular member 92 along with the advance of the manipulation wire 6, advances the distal end of the coil spring 9, and the locking of the holding tube 3 onto the sheath distal end member 50 is released, the engaged and disengaged states between the holding tube 3 and the sheath distal end member 50 is capable of being switched only by the advance and retraction of the manipulation wire 6.

Second Embodiment

Figure 7:
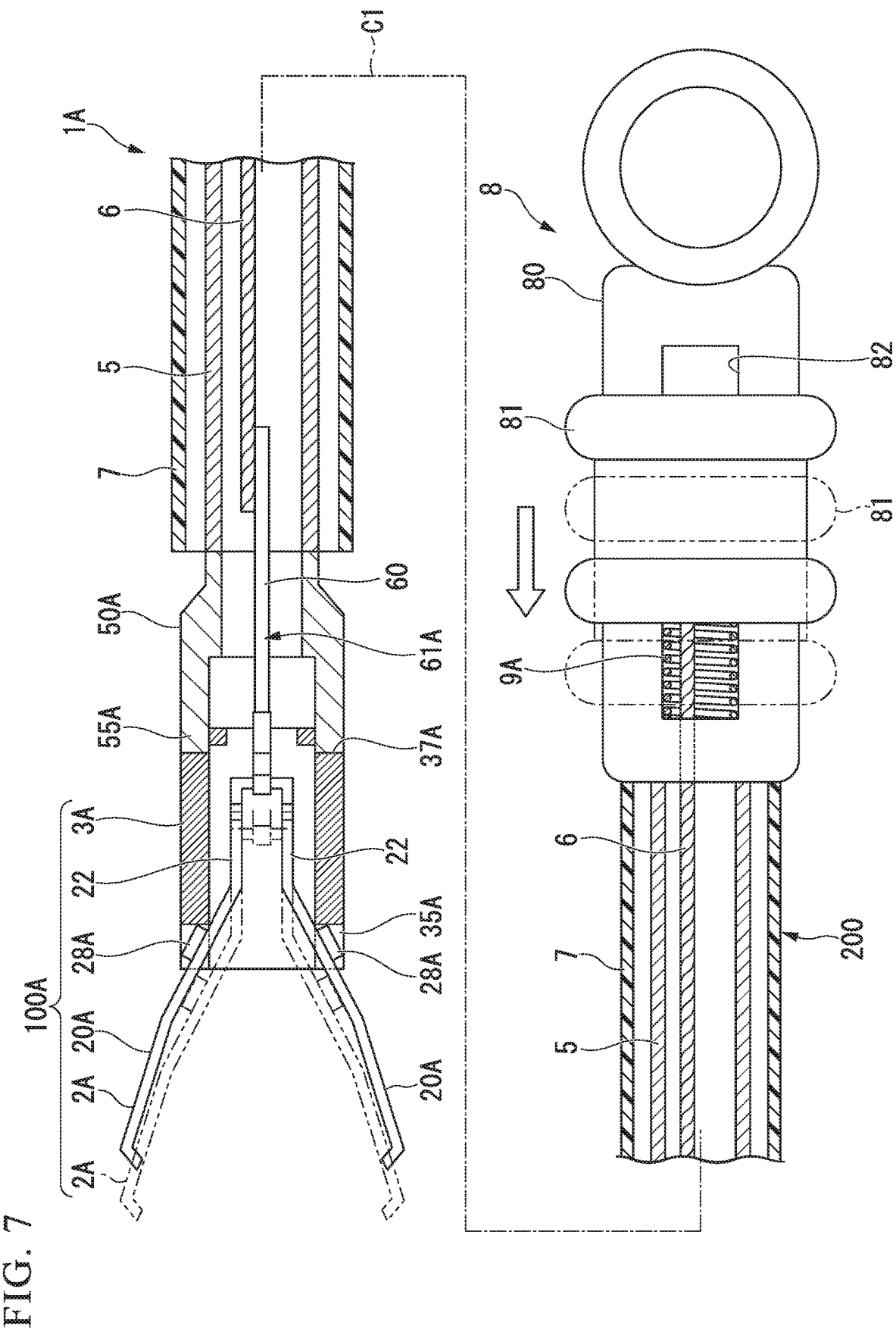
FIG. 7 is a sectional view of an endoscopic surgical device according to a second embodiment of the present invention.

An endoscopic surgical device 1A according to a second embodiment will be described with reference to FIGS. 7 to 9. In the embodiment to be described below, the same components as those of the aforementioned endoscopic surgical device 1 according to the first embodiment in view of the function or structure are given the same reference signs as in the above embodiment, and description overlapping with the above embodiment will be omitted.

In the endoscopic surgical device 1A according to the present embodiment, constitutions of a holding tube, a sheath distal end member, a coil spring, and a coupler are different from those of the first embodiment. FIG. 7 is a sectional view of an endoscopic surgical device 1A according to the present embodiment. FIG. 8 is a side view illustrating a proximal portion of a holding tube 3A and a sheath distal end member 50A. FIG. 9 is a side view illustrating a distal end of the holding tube 3A of the present embodiment. FIG. 10 is a schematic view illustrating a locking structure between the holding tube 3A and arms 20A of the present embodiment, and illustrates the holding tube 3A as seen from a distal end side in the direction of the longitudinal axis C1.

Figure 8:
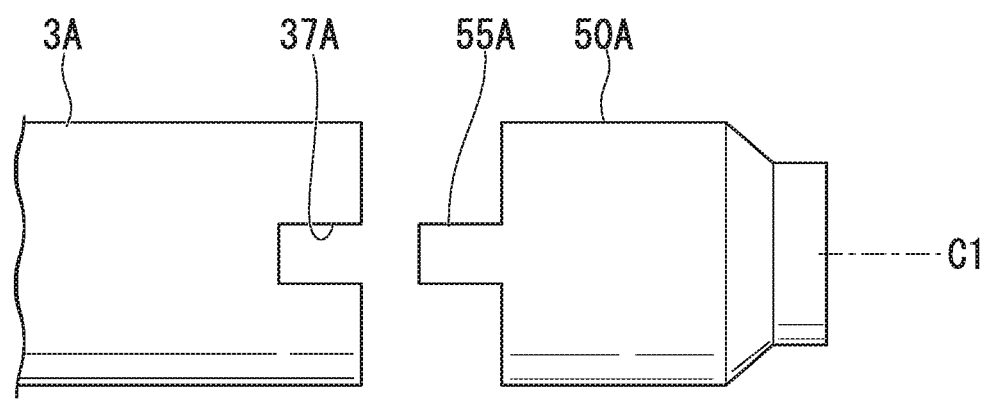
FIG. 8 is a side view of an engagement structure between a holding tube and a sheath distal end member in the second embodiment.

As illustrated in FIG. 8, slits 37A that extend from a proximal end of the holding tube 3A in the direction of the longitudinal axis C1 are formed in the proximal portion of the holding tube 3A at two or more places in a circumferential direction of the holding tube 3A. Protrusions 55A that protrude from a distal end in the direction of the longitudinal axis C1 are formed on the sheath distal end member 50A in the same number as the number of the slits 37A. The protrusions 55A are inserted into the slits 37A, and the holding tube 3A is locked to be nonrotatable relative to a coil sheath 5. As a result, it is capable of switching a state in which the holding tube 3A is nonrotatably engaged with the sheath distal end member 50A and a state in which the engagement of the holding tube 3A with the sheath distal end member 50A is released and the clip body 2 is rotatable by the advance and retraction of the holding tube 3A.

Figure 9:
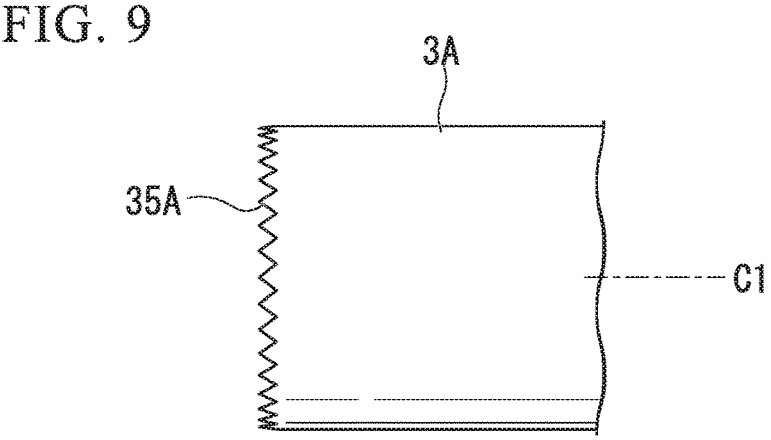
FIG. 9 is a side view illustrating a distal portion of the holding tube in the second embodiment.
Figure 10:
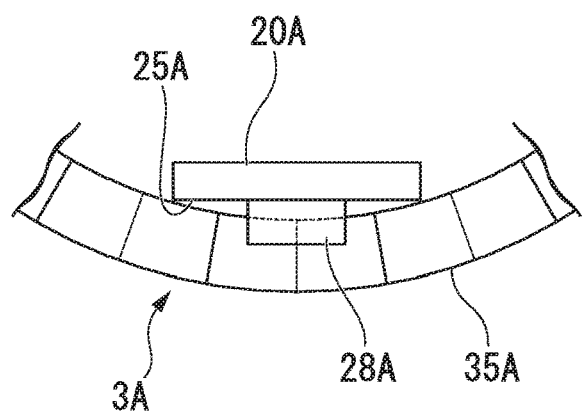
FIG. 10 is a schematic view illustrating a locking structure between arms and the holding tube in the second embodiment.

As illustrated in FIG. 9, a plurality of uneven parts 35A in which the distal end protrudes in a triangular shape in the direction of the longitudinal axis C1 are formed in the holding tube 3A of the present embodiment. As illustrated in FIG. 10, locking protrusions 28A that protrude in thickness directions T of the arms 20A are formed on outer surfaces 25A of the arms 20A. The locking protrusions 28A of the arms 20A are locked on one of the concave portions of the uneven parts 35A, and the arms 20A are locked on the holding tube 3A. To be specific, when a position of the clip body 2 relative to the holding tube 3A in the direction of the longitudinal axis C1 is a prescribed position, a state in which the locking protrusions 28A of the arms 20A are locked on the uneven parts 35A is maintained. As a result, the holding tube 3A rotates while following the rotation of the clip body 2A around the longitudinal axis C1. Meanwhile, during ligation, when the clip body 2A is pulled toward the proximal side, the arms 20A retract in the holding tube 3A, and the locking protrusions 28A of the arms 20A and the uneven parts 35A are unlocked, so that the arms 20A are closed.

In the present embodiment, the coil spring 9A is provided in a manipulator 8. The coil spring 9A is provided in a slide groove 83 of a manipulator body 80 and is provided on the distal side relative to a slider 81. A proximal end of the coil spring 9A is coupled to a distal portion of the slider 81, and a distal end of the coil spring 9A is coupled to a distal portion in the slide groove 83. The coil spring 9A is configured to bias the slider 81 toward the proximal side.

In the present embodiment, since the coil spring 9A is provided in the manipulator 8, the convex portion 64 and the tubular member 92 of the first embodiment are not provided on a coupler 61A.

An operation of the endoscopic surgical device 1A according to the present embodiment will be described.

The endoscopic surgical device 1A is configured such that, in a natural state in which no external load is applied, the slider 81 is biased toward the proximal side by a biasing force of the coil spring 9A, and a position of the manipulation wire 6 is maintained at an initial position. As a result, in the natural state, the manipulation wire 6 is biased toward the proximal side to be maintained at the initial position, and the arms 20A of the clip body 2 are locked on the slits 37A, so that the clip body 2 is held in a nonrotatable state.

Meanwhile, when the operator advances the slider 81, the coil spring 9 is compressed, and the manipulation wire 6 advances. The clip body 2 advances relative to the holding tube 3A in accordance with the advance of the manipulation wire 6, and the arms 20 are separated from the slits 37A, so that the locking of the clip body 2 onto the holding tube 3A is released. As a result, the clip body 2 is allowed to be rotatable relative to the holding tube 3A and the coil sheath 5 around the longitudinal axis C1, and an opening-closing direction of the anus 20 is capable of being adjusted to a desired direction.

When a load of a force toward the slider 81 is released, for example, by the operator relaxing the force applied to the slider 81, the slider 81 and the manipulation wire 6 retract to the initial position by a restoring force of the coil spring 9, return to the nonrotatable state, and the arms 20 are held in a desired opening-closing direction.

The present embodiment is different from the first embodiment in that, when the arms 20A are in the rotatable state, the engagement between the holding tube 3A and the sheath distal end member 50A is maintained. An aspect at the time of another manipulation is the same as the endoscopic surgical device 1 according to the first embodiment.

In the endoscopic surgical device 1A according to the present embodiment, as in the endoscopic surgical device 1 according to the first embodiment, in the state in which a load is not applied to the slider 81, the clip body 2 is held to be nonrotatable relative to the coil sheath 5 around the longitudinal axis C1. Therefore, manipulating the clip body 2 to rotate around the longitudinal axis C1 (the opening-closing direction of the arms) to match a desired direction is easily performed.

In the endoscopic surgical device 1A according to the present embodiment, for example in the case where claws 26 of the clip body 2 come into contact with the target tissue for treatment, the clip body 2A is capable of being prevented from rotating by receiving an external force to a distal end of the clip body 2A. Meanwhile, when the slider 81 is advanced, the clip body 2A is moved from the coil sheath 5 toward the distal side, the clip body 2A is allowed to be rotatable around the longitudinal axis C1. For this reason, in the endoscopic surgical device 1A, the clip body 2A is capable of being switched between the rotatable state and the nonrotatable state by simple manipulation, and the direction of the clip body 2A is easily adjusted. The endoscopic surgical device 1A has excellent manipulability.

While the embodiments of the present invention have been described in detail with reference to the figures, the specific constitution is not limited to the embodiments, and includes a change in the constitution without departing from the gist of the present invention.

For example, the clip body and the holding tube may be configured to rotate in the rotatable state using the holding tube 3 of the first embodiment in place of the holding tube 3A of the second embodiment.

In the first embodiment, the example in which the holding tube 3 is nonrotatably locked on the sheath distal end member 50 by the engagement between the proximal end face 32 of the holding tube 3 and the distal end face 51 of the sheath distal end member 50 is shown, but the locking structure between the holding tube 3 and the sheath distal end member 50 is not limited thereto. For example, the holding tube and the sheath distal end member may be configured to be relatively nonrotatably engaged by a frictional force. The others may be an aspect illustrated in FIG. 11.

Figure 11:
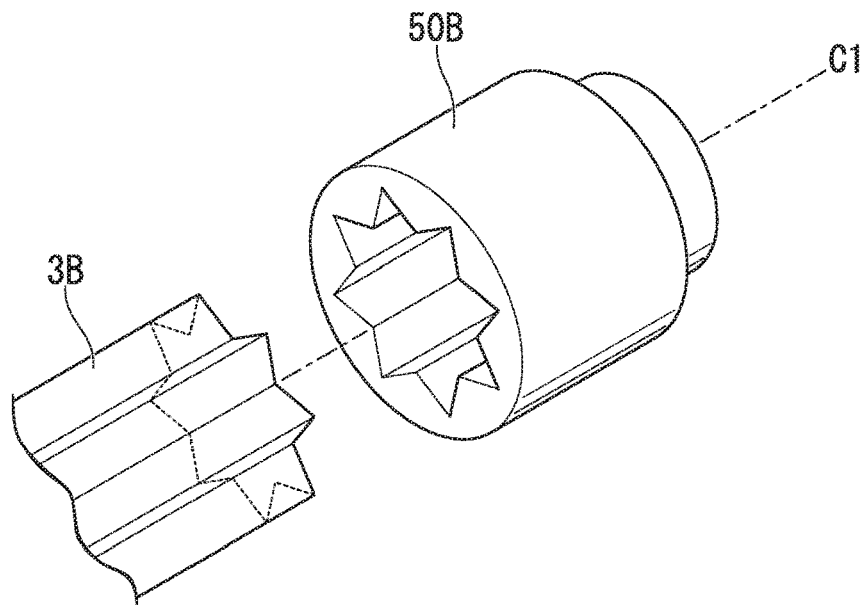
FIG. 11 is a perspective view illustrating a modified example of a locking structure between the holding tube and the sheath distal end member.

FIG. 11 is a perspective view illustrating a modified example of a locking structure between a holding tube 3B and a sheath distal end member SOB. The modified example illustrated in FIG. 11 is an example in which an indented surface is formed on an outer circumference of the holding tube 3B, and an inner circumferential surface of a lumen of the sheath distal end member SOB is formed to correspond to the indented surface of the outer circumference of the holding tube 3B. Even in the constitution, the endoscopic surgical device is capable of switching between a state in which the holding tube 3B nonrotatably engages with the sheath distal end member SOB and a state in which the engagement of the holding tube 3B with the sheath distal end member SOB is released and the clip body 2 is rotatable by the advance and retraction of the holding tube 3B.

In the first embodiment, the example in which the arms 20 are locked on the holding tube 3 by the covering part 31 of the holding tube 3, and the holding tube 3 follows the rotational operation of the clip body 2 is shown, but the locking structure between the holding tube 3 and the arms 20 of the clip body 2 is not limited thereto. For example, the locking structure may be an aspect illustrated in FIGS. 12 and 13.

Figure 12:
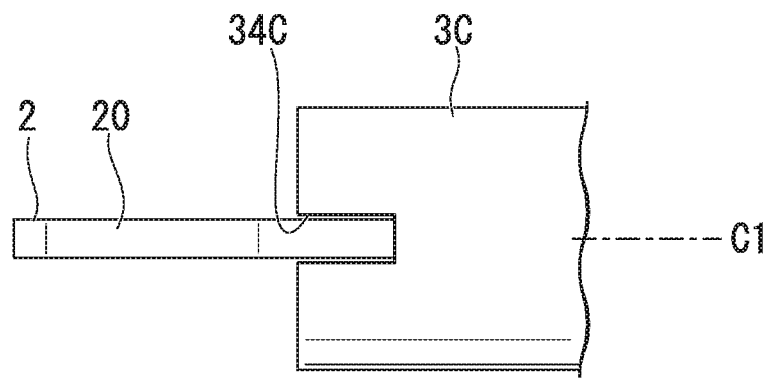
FIG. 12 is a side view illustrating a modified example of the locking structure between the arms and the holding tube of the first embodiment.
Figure 13:
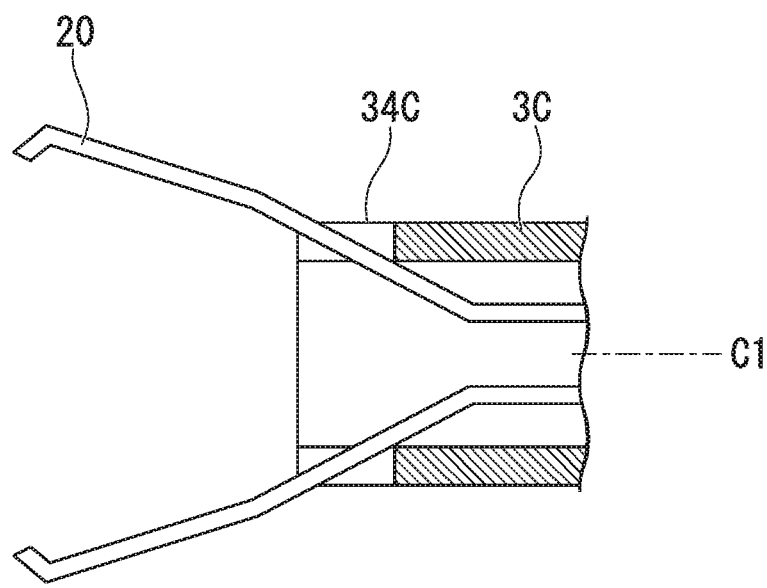
FIG. 13 is a partial sectional view illustrating the locking structure between the holding tube and the arms illustrated in FIG. 12.

FIG. 12 is a side view illustrating a modified example of the locking structure between the arms and the holding tube of the first embodiment. FIG. 13 is a partial sectional view illustrating the locking structure between the holding tube and the arms illustrated in FIG. 12. In this modified example, in place of the covering part 31, two distal end slits 34C extending in the direction of the longitudinal axis C1 are provided in a distal end of a tubular holding tube 3C across the longitudinal axis C1. The distal end slits 34C are formed in dimensions where arms 20 are inserted to be lockable. As illustrated in FIG. 12, when the arms 20 are in an expanded state and a position of the clip body 2 relative to the holding tube 3C in the direction of the longitudinal axis C1 is at a prescribed position, a state in which the arms 20 is locked inside the distal end slits 34C is maintained. As a result, the holding tube 3C rotates while following the rotation of the clip body 2 around the longitudinal axis C1. Meanwhile, during ligation, when the clip body 2 is pulled toward the proximal side, the arms 20 retract in the distal end slits 34C. When the arms 20 are closed, engagement of the arms 20 with the distal end slits 34C is released.

In the second embodiment, the example in which the protrusions 28A of the arms 20 are locked on the uneven parts 35A of the holding tube 3A, and the clip body 2 is nonrotatably locked on the holding tube 3A is shown, but the locking structure between the holding tube 3 and the arms 20 of the clip body 2 is not limited thereto. For example, the locking structure may be an aspect illustrated in FIGS. 14 and 15.

Figure 14:
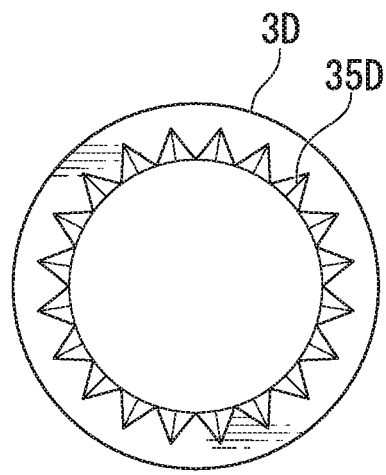
FIG. 14 is a front view illustrating a modified example of a distal portion of the holding tube of the second embodiment.
Figure 15:
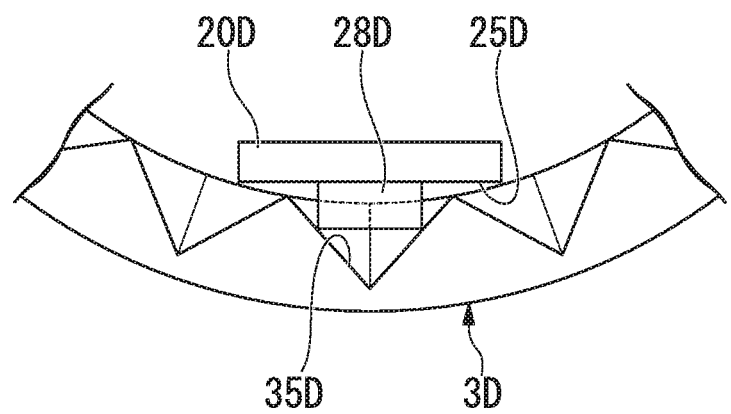
FIG. 15 is a schematic view illustrating a locking structure between the holding tube and the arms illustrated in FIG. 14.

FIG. 14 is a front view illustrating a modified example of a distal portion of a holding tube 3D. FIG. 15 is a schematic view illustrating a locking structure between the holding tube 3D and arms 20D illustrated in FIG. 14, and illustrates the holding tube 3D as seen from a distal end side in the direction of the longitudinal axis C1. As in the second embodiment illustrated in FIG. 10, locking protrusions 28D are formed at the arms 20D of this modified example. As illustrated in FIGS. 14 and 15, a plurality of triangular pyramid shaped concave portions 35D are formed in a boundary between a lumen and a distal end face at a distal end of the holding tube 3D in a circumferential direction. When a position of the clip body 2D relative to the holding tube 3D in the direction of the longitudinal axis C1 is at a prescribed position, a state in which the locking protrusions 28D of the arms 20D are locked on the concave portions 35D and the arms 20D are locked on the holding tube 3D is maintained. As a result, the clip body 2D is nonrotatable around the longitudinal axis C1. Meanwhile, when the clip body 2D advances relative to the holding tube 3D, the locking of the locking protrusions 28D onto the concave portions 35D is released, and the clip body 2D is rotatable around the longitudinal C1. During ligation, when the clip body 2D is pulled toward the proximal end side, the arms 20D retract in the holding tube 3D. When the arms 20D are closed, the locking between the locking protrusions 28D of the arms 20D and the uneven parts 35A is released.

The second embodiment and the modified example are configured such that the locking protrusions 28A and 28D are provided on the outer surfaces 25A and 25D of the arms 20A and 20D and the locking protrusions 28A and 28D and the uneven parts 35A and 35D are locked. However, in place of the locking protrusions 28A and 28D, holes are formed in the arms 20, and the holes may be configured to be locked on protrusions of the uneven parts 35A and 35D. In this case, the holes have shapes (for example, tapered triangular shapes), each of which has a tapered surface on a distal end side of an inner circumference. Thereby, when the arms are pulled toward the proximal end side, the locking between the holes and protrusions of the uneven parts 35A and 35D is released by the tapered surfaces.

In the embodiment, the example in which the stoppers 27 are formed to protrude from the opposite sides of the bases 22 of the pair of arms 20 is shown. However, the stoppers may be formed to extend and protrude from the outer surfaces 25 of the bases 22 in the direction perpendicular to the longitudinal axis C1.

In the embodiment, the example in which the clip unit is made of the clip body and the holding tube is shown, but the constitution of the clip unit is not limited thereto. For example, the clip unit may have a function of providing the coil spring in the holding tube and re-gripping the coil spring by the clip body. In the embodiment, the example in which the hook 62 is deformed when the engagement between the clip body 2 and the coupler 61 is released is shown, but the coupling structure between the coupler 61 and the clip body 2 is not limited thereto. As a modified example structure, a structure between the clip unit having the re-gripping function and the coupler will be described using a modified example of the endoscopic surgical device 1A of the second embodiment illustrated in FIGS. 16 to 18.

Figure 16:
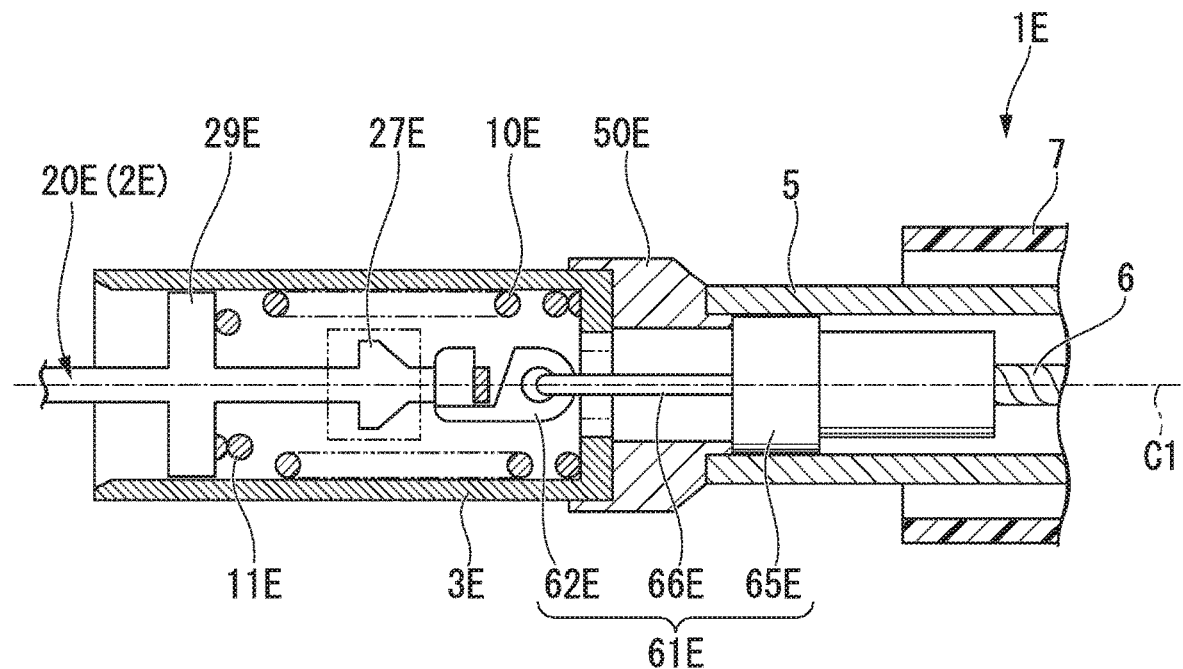
FIG. 16 is a sectional view illustrating a use mode of an endoscopic surgical device of a modified example of the second embodiment.
Figure 17:
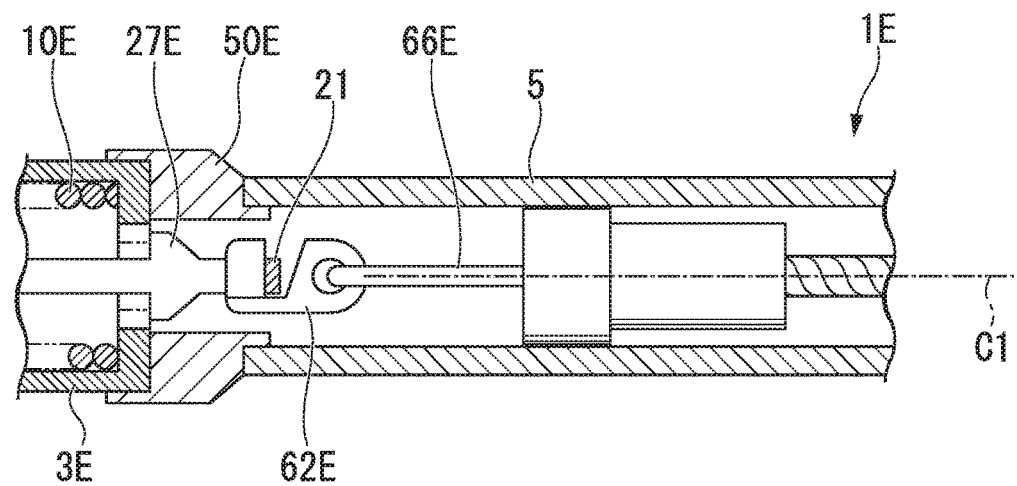
FIG. 17 is a sectional view illustrating a use mode of an endoscopic surgical device of a modified example of the second embodiment.
Figure 18:
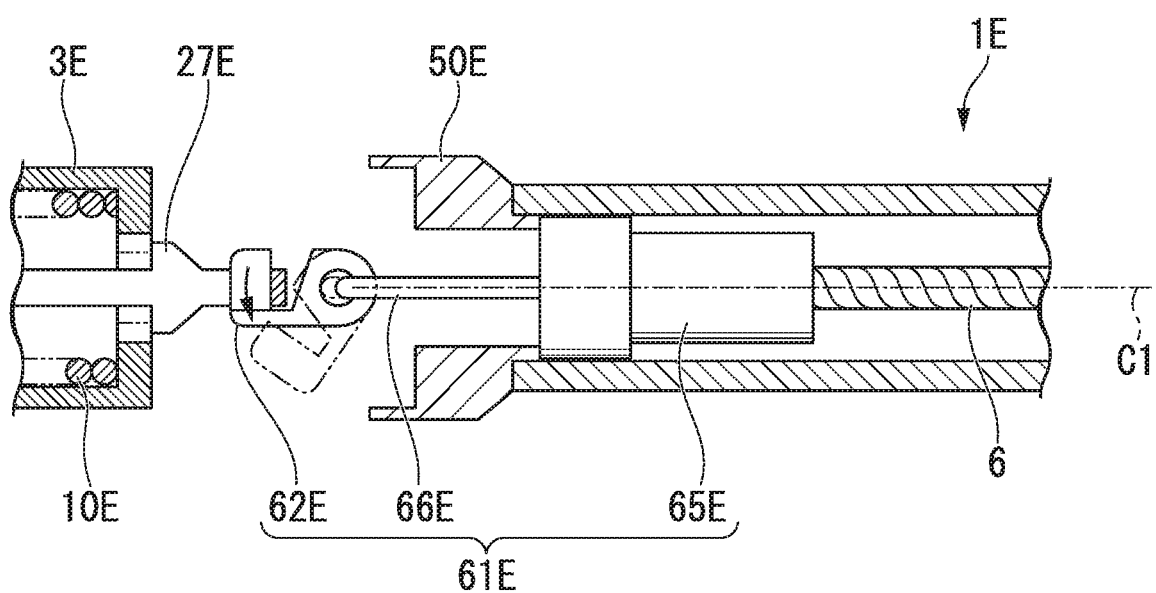
FIG. 18 is a sectional view illustrating a use mode of an endoscopic surgical device of a modified example of the second embodiment.

FIGS. 16 to 18 are sectional views illustrating a use mode of an endoscopic surgical device 1E of a modified example of the second embodiment. In the modified example, if stoppers are located in a lumen of a holding tube, re-gripping of the target tissue for treatment can be performed.

As illustrated in FIGS. 16 to 18, a coil spring 10E is inserted into a holding tube 3E. The coil spring 10E is disposed coaxially with the holding tube 3E, and approaches an inner circumferential surface of the holding tube 3E. A clip body 2E and a coupler 61E are inserted on an inner circumferential side of the coil spring 10E.

Spring stoppers 29E are provided more toward a distal end side of the clip body 2E than stoppers 27E. The spring stoppers 29E protrude from sides of arms 20E in a direction perpendicular to the longitudinal axis C1.

The coil spring 10E is disposed between a proximal end face of a lumen of the holding tube 3E and the spring stoppers 29E. A proximal portion of the coil spring 10E and the proximal end face of the lumen of the holding tube 3E may be fixed by welding or the like, or may not be fixed. The coil spring 10E may have a coiled seat 11E in which a distal portion thereof is configured to have a smaller inner diameter than the other portion.

The coupler 61E includes a hook 62E, a columnar proximal portion 65E, and a loop wire 66E. A distal end of the manipulation wire 6 is inserted into and joined to the proximal portion 65E. A proximal end of the loop wire 66E is inserted into and joined to a distal end of the proximal portion 65E. A through-hole 63E is formed at a proximal end of the hook 62E, and the loop wire 66E is inserted thereinto. For this reason, the hook 62E is rotatably coupled to the loop wire 66E. The hook 62E is locked on a connector 21 of the clip body 2E. In a state in which a tensile force is applied to the manipulation wire 6 and the coupler 61E, a locking state between the hook 62E and the connector 21 of the clip body 2E is maintained.

When the operator moves a slider 81 toward a distal end side relative to a manipulator body 80 in order to re-grip the target tissue for treatment, the compressed coil spring 10E is expanded. That is, when the slider 81 is moved toward the distal end side relative to the manipulator body 80, the clip body 2E moves toward the distal end side of the holding tube 3E by an action of the coil spring 10E, and the arms 20E return to an expanded state.

After the arms 20E returns to an expanded state, the arms 20E face another target tissue for treatment, for example, by bending a curvature of the endoscope. Hereinafter, the aforementioned steps are performed, and the target tissue for treatment can be re-gripped by a clip unit 100E.

Like the endoscopic surgical device 1 of the first embodiment, after the target tissue for treatment is ligated by the clip body 2E, the slider 81 is retracted toward the proximal end side until the stoppers 27E are locked on a proximal end face of the holding tube 3E, and then the clip body 2E is fixed to the holding tube 3E (see FIG. 17). When the operator moves the manipulation wire 6 toward the distal end side in a state in which the clip body 2E is fixed to the holding tube 3E, the loop wire 66E advances relative to the coupler 61E, and the hook 62E is rotatable, so that locking between the hook 62E and the connector 21E is released. The following manipulation is the same as in the second embodiment.

Although the embodiments of the present invention have been described, the technical scope of the present invention is not limited to the embodiments, and can change a combination of the components in the embodiments, apply various changes to each component, or eliminate each component without departing from the scope of the present invention. The present invention is not limited to the above description, but it is limited only by the appended claims.

What is claimed is:

1. An endoscopic surgical device comprising:
   a sheath;
   a manipulator provided at a proximal end of the sheath;
   a manipulation wire that is inserted through the sheath and includes a proximal end that is coupled to the manipulator;
   a clip body having a pair of openable and closeable arms and connected to a distal end of the manipulation wire, the clip body being configured to advance and retract in accordance with manipulation of the manipulator in a direction of a longitudinal axis of the manipulation wire;
   a holding tube into which a proximal portion of the clip body is inserted so as to be capable of advancing and retracting inside of the holding tube; and
   a biasing member configured to hold a position of the manipulation wire at an initial position,
   wherein the manipulation wire is configured to be advanced by a prescribed amount against a biasing force of the biasing member to move from: (i) the initial position at which the clip body is configured to be non-rotatable around the longitudinal axis with respect to the sheath to (ii) a second position at which the clip body is configured to be rotatable around the longitudinal axis with respect to the sheath such that an opening-closing direction of the pair of arms can be adjusted.

2. The endoscopic surgical device according to claim 1, wherein when the clip body is rotatable around the longitudinal axis, the holding tube is locked on the clip body so as to rotate while following a rotation of the clip body.

3. The endoscopic surgical device according to claim 2, wherein the biasing member is disposed at a distal portion of the sheath.

4. The endoscopic surgical device according to claim 3, further comprising:
- a tubular member to which a distal end of the biasing member is connected and through which the manipulation wire is inserted; and
- a convex portion provided to protrude from an outer circumference of the manipulation wire, wherein:
- a proximal end of the biasing member is fixed to the distal portion of the sheath, and
- during advancement and retraction of the manipulation wire, the convex portion and the tubular member are configured to come into contact with each other, and the distal end of the biasing member is configured to advance and retract.

5. The endoscopic surgical device according to claim 2, further comprising:
- a tubular member to which a distal end of the biasing member is connected and through which the manipulation wire is inserted; and
- a convex portion provided to protrude from an outer circumference of the manipulation wire, wherein:
- a proximal end of the biasing member is fixed to a distal portion of the sheath, and
- during advancement and retraction of the manipulation wire, the convex portion and the tubular member are configured to come into contact with each other, and the distal end of the biasing member is configured to advance and retract.

6. The endoscopic surgical device according to claim 1, wherein, when the manipulation wire is in the second position, the clip body is rotatable around the longitudinal axis, axis with respect to the sheath while the holding tube is locked on a distal portion of the sheath to be non-rotatable around the longitudinal axis.

7. The endoscopic surgical device according to claim 6, wherein: the manipulator includes: a manipulator body; and a slider which is slidable relative to the manipulator body and to which the manipulation wire is coupled; and the biasing member is provided in the manipulator body and is configured to bias the slider toward a proximal end side such that the biasing member is capable of holding the manipulation wire at the initial position.

8. The endoscopic surgical device according to claim 1, wherein the manipulation wire is rotatable around the longitudinal axis with respect to the sheath.

9. The endoscopic surgical device according to claim 1, wherein the holding tube is configured to:
- contact a distal portion of the sheath so as to be non-rotatable around the longitudinal axis with respect to the sheath when the manipulation wire is held at the initial position by the biasing member, and
- move apart from the distal portion of the sheath so as to become rotatable around the longitudinal axis with respect to the sheath when the manipulation wire is advanced against the biasing force of the biasing member to the second position.

10. The endoscopic surgical device according to claim 9, wherein the holding tube is configured to advance along the longitudinal axis following advancement of the clip body along the longitudinal axis.

11. The endoscopic surgical device according to claim 9, wherein the holding tube comprises a part that couples the holding tube to the clip body in a manner such that holding tube is configured to advance along the longitudinal axis following advancement of the clip body along the longitudinal axis.

* * * * *